US00PP26008P3

(12) United States Plant Patent
Klemm et al.

(10) Patent No.: US PP26,008 P3
(45) Date of Patent: Oct. 20, 2015

(54) POINSETTIA PLANT NAMED 'NPCW14227'

(50) Latin Name: *Euphorbia pulcherrima*
Varietal Denomination: NPCW14227

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 143 days.

(21) Appl. No.: 13/999,089

(22) Filed: Jan. 9, 2014

(65) Prior Publication Data
US 2015/0195983 P1 Jul. 9, 2015

(51) Int. Cl.
*A01H 5/00* (2006.01)

(52) U.S. Cl.
USPC ..... Plt./307

(58) Field of Classification Search
USPC ..... Plt./307
See application file for complete search history.

*Primary Examiner* — Annette Para
(74) *Attorney, Agent, or Firm* — Barbara Campbell; James M. Weateherly; Cochran Freund & Young, LLC

(57) ABSTRACT

A new poinsettia plant particularly distinguished by having pinkish-red bracts, dark green foliage, a triangular plant form, and an upright growth habit, is disclosed.

1 Drawing Sheet

Genus and species: *Euphorbia pulcherrima.*
Variety denomination: 'NPCW 14227'.

BACKGROUND OF THE NEW PLANT

The present invention comprises a new and distinct variety of poinsettia, botanically known as *Euphorbia pulcherrima* and hereinafter referred to by the variety name 'NPCW14227'. 'NPCW14227' was derived as a selection from a controlled cross conducted in Nairobi, Kenya in November/December 2008 between the proprietary female parent 'SK 63' (unpatented) having white bracts and light green foliage and the proprietary male parent 'SK 66' having red bracts and dark green foliage.

In November 2009, a single plant was selected in Stuttgart, Germany from plants produced from the initial cross. In May 2010, 'NPCW14227' was first asexually propagated by vegetative cuttings. 'NPCW 14227' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Pinkish-red bracts;
2. Dark green foliage; and
3. A triangular plant form and an upright growth habit.

DESCRIPTION OF THE PHOTOGRAPH

This new poinsettia plant is illustrated by the accompanying photograph which shows an overall view of the plant. The photograph is of a plant approximately four-months-old grown indoors in Stuttgart, Germany in November 2012. The colors shown are as true as can be reasonably obtained by conventional photographic procedures.

DESCRIPTION OF THE NEW VARIETY

The following detailed descriptions set forth the distinctive characteristics of 'NPCW14227'. The data which define these characteristics were collected from asexual reproductions carried out in Stuttgart, Germany. Data was collected on four-month-old plants grown indoors in Stuttgart, Germany under greenhouse conditions in the fall of 2013. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW 14227'.

Parentage:
- *Female.*—Proprietary poinsettia parent 'SK 63' (unpatented).
- *Male.*—Proprietary poinsettia parent 'SK 66' (unpatented).

Growth:
- *Time to produce a rooted cutting.*—4 weeks.
- *Blooming habit.*—Intermittent.
- *Flowering response time.*—Approximately 49 days.
- *Keeping quality.*—Good.

Plant description:
- *Form.*—Triangular.
- *Growth habit.*—Upright.
- *Height.*—30.0 cm to 32.0 cm.
- *Width.*—32.0 cm to 35.0 cm.
- *Number of branches.*—5 to 6.
- *Average number of inflorescences per plant.*—5.5.

Propagation:
- *Type cuttings.*—Apical cuttings.
- *Time to produce a rooted cutting.*—4 weeks.

Stems:
*Color*.—RHS 143A.
*Length*.—27.0 cm.
*Internode length*.—1.5 cm to 3.5 cm.
*Diameter*.—0.4 cm to 0.6 cm.

Leaves:
*Quantity*.—6 to 8 per lateral branch.
*Arrangement*.—Alternate.
*Shape*.—Ovate.
*Apex*.—Acute.
*Base*.—Obtuse.
*Margin*.—Serrate.
*Length*.—9.0 cm to 12.0 cm.
*Width*.—6.0 cm to 8.0 cm.
*Lobes*.—Lobation characteristics: Shallow.
*Texture* (*both surfaces*).—Smooth.
*Vein color*.—Upper surface: Transparent. Lower surface: RHS 139D; middle vein is slightly reddish.
*Variegation*.—Absent.
*Color*.—Mature foliage: Upper surface: RHS 139A. Lower surface: RHS 139D. Immature foliage: Upper surface: RHS 141A. Lower surface: RHS 139B.
*Leaf petiole*.—Length: 3.0 cm to 6.0 cm. Diameter: 0.2 cm to 0.3 cm. Color: Upper (part) surface: RHS 185A. Lower (part) surface: RHS 182B.

Inflorescence:
*Lastingness of inflorescence on the plant*.—3 to 4 weeks.
*Diameter*.—17.0 cm to 20.0 cm.
*Height*.—3.0 cm to 4.0 cm.
*Fragrance*.—Absent.

Bracts:
*Number of bracts per inflorescence*.—8 to 10.
*Shape*.—Ovate.
*Apex*.—Acute.
*Base*.—Obtuse.
*Margin*.—Entire to slightly serrate.
*Size*.—Length: 5.0 cm to 9.0 cm. Width: 4.0 cm to 5.0 cm.
*Texture* (*both upper and lower surfaces*).—Smooth.
*Vein color*.—Upper surface: RHS 185A. Lower surface: RHS 182B.
*Bract color* (*both upper and lower surfaces*).—RHS 50A.
*Bract petiole*.—Length: 0.5 cm to 2.5 cm. Diameter: 0.2 cm. Color: Upper (part) surface: RHS 185A. Lower (part) surface: RHS 182B.

Cyme:
*Diameter*.—0.5 cm to 1.2 cm.
*Cyathia number*.—3 to 4 per inflorescence.
*Cyathium*.—Shape: Ovate. Diameter: 0.2 cm to 0.4 cm. Length: 0.3 cm to 0.5 cm. Color: RHS 143C.
*Peduncle*.—Color: RHS 142B. Length: 0.2 cm to 0.25 cm.
*Nectar cups*.—Number: 1 per cyathium. Diameter: 0.1 cm. Size: 0.3 cm to 0.4 cm. Color: RHS 1C.

Reproductive organs: Not observed.
Fruit and seed set: None observed.
Disease and pest resistance: None observed.

COMPARISON WITH PARENTAL LINE AND KNOWN VARIETY

'NPCW 14227' is a distinct variety of poinsettia having pinkish-red bracts. 'NPCW 14227' is distinguished from its parents as described in Table 1.

TABLE 1

| Characteristic | Variety 'NPCW14227' | Female Parent 'SK 63' | Male Parent 'SK 66' |
|---|---|---|---|
| Bract color | Pinkish red | White | Red |
| Foliage color | Dark green | Light green | Dark green |

'NPCW 14227' can be compared to the commercial poinsettia plant variety CHRISTMAS FEELINGS™ 'Neon' (unpatented). Differences between the two varieties are described in Table 2.

TABLE 2

| Comparison with Similar Variety | | |
|---|---|---|
| Characteristic | 'NPCW14227' | Commercial line CHRISTMAS FEELINGS ™ 'Neon' |
| Vigor | More vigorous than CHRISTMAS FEELINGS ™ 'Neon' | Less vigorous than 'NPCW14227' |
| Earliness to flower | One week earlier than CHRISTMAS FEELINGS ™ 'Neon' | One week later than 'NPCW14227' |

We claim:

1. A new and distinct variety of poinsettia plant named 'NPCW14227' as shown and described herein.

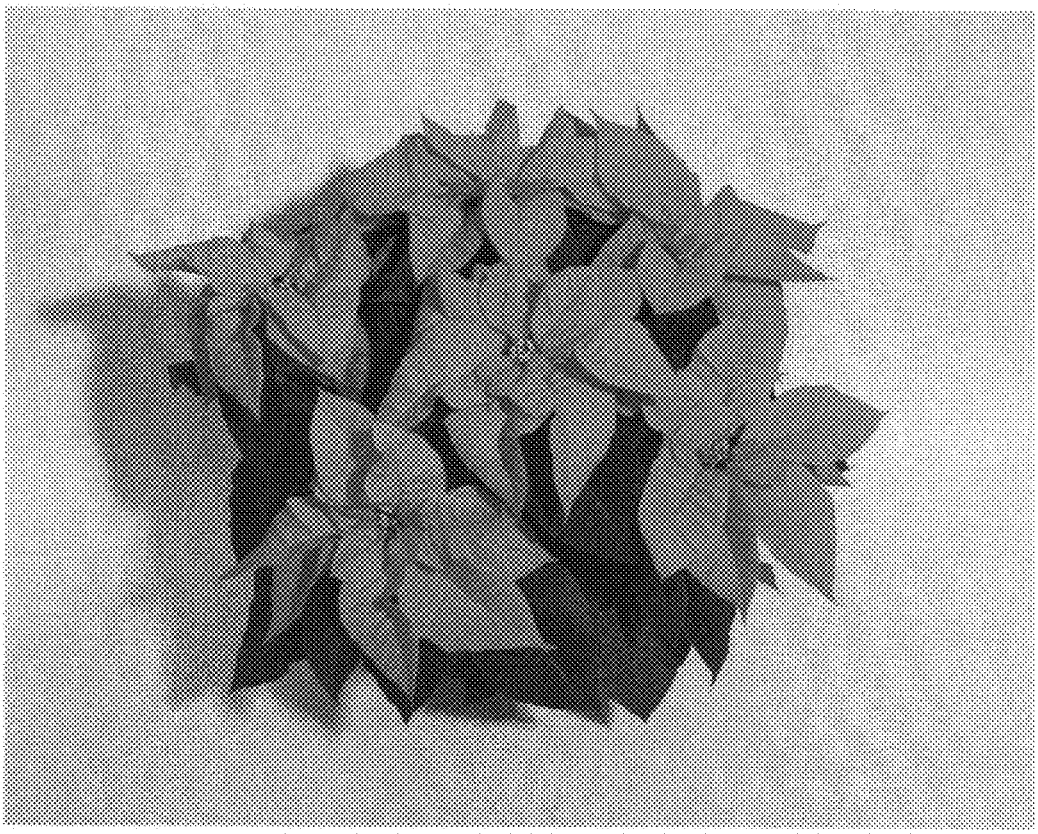

* * * * *